United States Patent
Citron et al.

(10) Patent No.: US 6,331,550 B1
(45) Date of Patent: *Dec. 18, 2001

(54) METHODS OF USE OF QUINOLONE COMPOUNDS AGAINST ANAEROBIC PATHOGENIC BACTERIA

(75) Inventors: Diane M. Citron; Ellie J. C. Goldstein, both of Santa Monica, CA (US)

(73) Assignee: SmithKline Beecham Corporation, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/400,144

(22) Filed: Sep. 21, 1999

Related U.S. Application Data

(60) Provisional application No. 60/141,458, filed on Jun. 29, 1999.

(51) Int. Cl.[7] ............................ A61K 31/47; A61K 31/44
(52) U.S. Cl. ............................ 514/312; 514/311; 514/300
(58) Field of Search .................................. 514/312, 311, 514/300

(56) References Cited

FOREIGN PATENT DOCUMENTS 0 688 772 A1   12/1995   (EP).
WO 98/42705    1/1998    (WO).

OTHER PUBLICATIONS

Citron, et al., "Frequency of Isolation of Porphyromonas Species from Infected Dog and Cat Bite Wounds in Humans and Their Characterization by Biochemical Tests and Arbitrarily Primed–Polymerase Chain Reaction Fingerprinting," *Clinical Infectious Diseases*, 23(S1): S78–S82 (1996).

Cormicon, et al., "Antimicrobial Activity and Spectrum of LB20304, a Novel Fluoronaphthyridone," *Antimicrobial Agents and Chemotherapy*, 41(1): 204–211 (1997).

Hohl, et al., "International multicenter investigation of LB20304, a new fluoronaphthyridone," *Clinical Microbiology and Infection*, 4(5):280–284 (1998).

Marco, et al., "Antimicrobial activity of LB20304, a fluoronaphthyridone, tested against anaerobic bacteria," *Journal of Antimicrobial Chemotherapy*, 40: 605–607 (1997).

Alexander, et al. "Characterization of Saccharolytic Bacteroides and Prevotella Isolates from Infected Dog and Cat Bite Wounds in Humans," *Journal of Clinical Microbiology*, 35(2): 406–411 (1997).

National Committee for Clinical Laboratory Standards, 17(2), M7–A4 (1997).

Summanen, et al., Wadsworth Anaerobic Bacteriology Manual, 5th ed.: 4,8 (1993).

Holdeman, et al., Anaerobic Laboratory Manual, 4th ed.: 49–63 (1977).

*Primary Examiner*—Kevin E. Weddington
(74) *Attorney, Agent, or Firm*—Loretta J. Henderson; Edward R. Gimmi; William T. King

(57) ABSTRACT

This invention relates, in part, to newly identified methods of using quinolone antibiotics, particularly a gemifloxacin compound against pathogenic bacteria, especially anaerobic pathogens.

16 Claims, No Drawings

METHODS OF USE OF QUINOLONE COMPOUNDS AGAINST ANAEROBIC PATHOGENIC BACTERIA

This application claims the benefit of provisional Ser. No. 60/141,458 filed Jun. 29, 1999.

This invention relates, in part, to newly identified methods of using quinolone antibiotics, particularly a gemifloxacin compound against anaerobic bacteria, especially unusual anaerobic bacteria

BACKGROUND OF THE INVENTION

Quinolones have been shown to be effective to varying degrees against a range of certain anaerobic pathogens. However, as diseases caused by these pathogens are on the rise, there exists a need for antimicrobial compounds that are more potent than the present group of quinolones.

Gemifloxacin mesylate (SB-265805) is a novel fluoroquinolone useful as a potent antibacterial agent. Gemifloxacin compounds are described in detail in patent application PCT/KR98/00051 published as WO 98/42705. Patent application EP 688772 discloses novel quinoline(naphthyridine) carboxylic acid derivatives, including anhydrous (R,S)-7-(3-aminomethyl-4-methoxyiminopyrrolidin-1-yl)-1-cyclopropyl-6-fluoro-4-oxo-1,4-dihydro-8-naphthyridine-3-carboxylic acid of formula I.

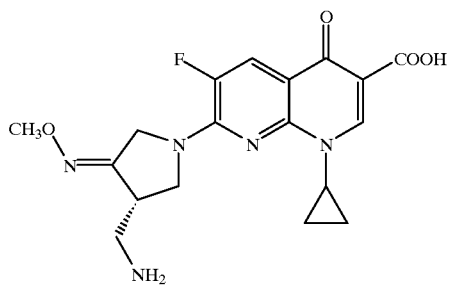

I

PCT/KR98/00051 discloses (R,S)-7-(3-aminomethyl-4-syn-methoxyimino-pyrrolidin-1-yl)-1-cyclopropyl-6-fluoro-4-oxo-1,4-dihydro-1,8-naphthyridine-3-carboxylic acid methanesulfonate and hydrates thereof including the sesquihydrate.

While in vitro testing of new antimicrobial compounds is often extensive, these studies tend to focus on a limited range of typical anaerobic bacterial pathogens (Cormicon, et al., *Antimicrob. Agents Chemother.*, 41:204–211, 1997; Hohl, et al., *Clin. Microbiol. Infect.*, 4:280–284, 1998; Marco, et al., *J. Antimicrob. Chemother.*, 40:605–607, 1997). Moreover, it has been reported that (Goldstein, et al., *Antimicrob. Agents Chemother.*, Submitted) the activity of gemifloxacin against typical anaerobic bacteria; it showed activity against *Bacteroides fragilis* and certain Prevotella and Porphyromonas strains, but only limited activity against *B. thetaiotaomicron*, *B. distasonis* and *B. ovatus*. Data is lacking about the activities of new quinolone compounds against many of the less frequently encountered anaerobic pathogens, such as Actinomyces spp., Anaerobiospirrilum spp., Porphyromonas spp., and *Bilophila wadsworthia*.

Provided herein is an invention based, in part, on a significant discovery made using a gemifloxacin compound against various unusual, though medically impotant, anaerobic bacteria, demonstrating the activity of the gemifloxacin compound used was superior to a number of quinolones as described in more detail herein. Gemifloxacin compounds are valuable compounds for the treatment of bacterial caused by a range of anaerobic pathogens, including those resistant to usual oral therapy, thereby filling an unmet medical need.

SUMMARY OF THE INVENTION

An object of the invention is a method for modulating metabolism of anaerobic pathogenic bacteria comprising the step of contacting anaerobic pathogenic bacteria with an antibacterially effective amount of a composition comprising a quinolone, particularly a gemifloxacin compound, or an antibacterially effective derivative thereof.

A further object of the invention is a method wherein said anaerobic pathogenic bacteria is selected from the group consisting of: a member of the genus Peptostreptococci, a *Peptostreptococci asaccharolyticus*, a *Peptostreptococci magnus*, a *Peptostreptococci micros*, a *Peptostreptococci prevotii*, a *Porphyromonas asaccharolytica*, a *Porphyromonas canoris*, a *Porphyromonas gingivalis*, a *Porphyromonas macaccae*, a member of the genus Actinomyces, an *Actinomyces israelii*, an *Actinomyces odontolyticus*, a member of the genus Clostridium, a *Clostridium innocuum*, a *Clostridium clostridioforme*, a *Clostridium difficile*, a member of the genus Anaerobiospirillum, a *Bacteroides tectum*, a *Bacteroides ureolyticus*, a *Bacteroides gracilis* (*Campylobacter gracilis*), a *Prevotella intermedia*, a *Prevotella heparinolytica*, a *Prevotella oris-buccae*, a *Prevotella bivia*, a *Prevotella melaninogenica*, a member of the genus Fusobacterium, a *Fusobacterium naviforme*, a *Fusobacterium necrophorum*, a *Fusobacterium varium*, a *Fusobacterium ulcerans*, a *Fusobacterium russii*, a member of the genus Bilophila, a *Bilophila wadsworthia*.

Also provided by the invention is a method of treating or preventing a bacterial infection by anaerobic pathogenic bacteria comprising the step of administering an antibacterially effective amount of a composition comprising a quinolone, particularly a gemifloxacin compound to a mammal suspected of having or being at risk of having an infection with anaerobic pathogenic bacteria.

A preferred method is provided wherein said modulating metabolism is inhibiting growth of said bacteria or killing said bacteria.

A further preferred method is provided wherein said contacting said bacteria comprises the further step of introducing said composition into a mammal, particularly a human.

Further preferred methods are provided by the invention wherein said bacteria is selected from the group consisting of: a member of the genus Peptostreptococci, a *Peptostreptococci asaccharolyticus*, a *Peptostreptococci magnus*, a *Peptostreptococci micros*, a *Peptostreptococci prevotii*, a member of the genus Porphyromonas, a *Porphyromonas asaccharolytica*, a *Porphyromonas canoris*, a *Porphyromonas gingivalis*, a *Porphyromonas macaccae*, a member of the genus Actinomyces, an *Actinomyces israelii*, an *Actinomyces odontolyticus*, a member of the genus Clostridium, a *Clostridium innocuum*, a *Clostridium clostridioforme*, a *Clostridium difficile*, a member of the genus Anaerobiospirillum, a member of the genus Bacteroides, a *Bacteroides tectum*, a *Bacteroides ureolyticus*, a *Bacteroides gracilis* (*Campylobacter gracilis*), a member of the genus Prevotella, a *Prevotelia intermedia*, a *Prevotella heparinolytica*, a *Prevotella oris-buccae*, a *Prevotella bivia*, a *Prevotella melaninogenica*, a member of the genus Fusobacterium, a *Fusobacterium naviforme*, a *Fusobacterium necrophorum*, a *Fusobacterium varium*, a *Fusobacte-* rium ulcerans, a Fusobacterium russii, a member of the genus Bilophila, a Bilophila wadsworthia.

Various changes and modifications within the spirit and scope of the disclosed invention will become readily apparent to those skilled in the art from reading the following descriptions and from reading the other parts of the present disclosure.

DESCRIPTION OF THE INVENTION

The present invention provides, among other things, methods for using a composition comprising a quinolone, particularly a gemifloxacin compound against anaerobic bacteria.

As used herein "gemifloxacin compound(s)" means a compound having antibacterial activity described in patent application PCT/KR98/00051 published as WO 98/42705, or patent application EP 688772.

This invention was based, in part, on analyses evaluating the comparative activity of gemifloxacin against various anaerobic pathogens. Since anaerobic susceptibility testing is not routinely performed in most clinical laboratories, if it is performed at all, the clinician must rely on published studies to help guide both empirical therapy as well as specific therapy in situations that involve less commonly isolated or identified anaerobes or mixed infections at other sites. Most in vitro studies of gemifloxacin against anaerobic bacteria focus their attention on common intra-abdominal pathogens such as *Bacteroides fragilis* and *Clostridium perfringens* or lump the anaerobes into large groups without speciation (Cormicon, et al., *Antimicrob.* Agents Chemother., 41:204–211, 1997; Marco, et al.,*J. Antimicrob. Chemother.*, 40:605–607, 1997). Consequently there is unmet medical need for data regarding certain species often recovered from respiratory and gynecological infections as well as less frequently identified components of mixed abdominal infections, as well as methods used for ther treatment of such pathogens.

The present invention was based, in part, on analyses showing that gemifloxacin compared favorably with trovafloxacin against the Gram-positive anaerobes tested as well as the other unusual isolates studied [see, for example, Table 1]. Cormicon and Jones (Cormicon, et al., *Antimicrob. Agents Chemother.*, 41:204–211, 1997) studied 10 strains of peptostreptococci and found an MIC$_{90}$ of 2 ug/ml for gemifloxacin which is in contrast to our study which included 45 strains of peptostreptococci from 4 species, all of which were susceptible to ≤ 0.25 ug/ml of gemifloxacin. The reason for this discrepancy can not be accounted for by methodological variations since both studies used brucella agar and an agar dilution method. Marco, et al. (Marco et al. *J. Antimicrob. Chemother.*, 40:605–607, 1997) studied 18 strains of peptostreptococci and also found an MIC$_{90}$ of 2 ug/ml [range, ≤ 0.25–8 ug/ml] for gemifloxacin.

Differences in the susceptibility of different Clostridium species to gemifloxacin were apparent in assays described herein, with *C. clostridioforme* and *C. innocuum* being relatively susceptible while *C. difficile* was often resistant to gemifloxacin. In the current study, the ten *C. ramosum* isolates studied had an MIC$_{90}$ of 1 ug/ml while a prior study (Goldstein, et al., *Antimicrob. Agents Chemother*, Submitted) the MIC$_{90}$ for the 14 isolates studied was 8 ug/ml. With the exception of two strains, all isolates in these two studies were different and most came from blood cultures. The apparent disparity comes from the higher MICs of 3/14 strains in the prior study and highlights the problem of testing small numbers of isolates of a single species, which has been solved by the analyses underpinning certain embodiments of the current invention. Further, Cormicon and Jones (Cormicon, et al., *Antimicrob. Agents Chemother.*, 41:204–211, 1997) studied ten clostridial isolates and found a maximum MIC of 2 ug/ml to gemifloxacin Marco, et al. (Marco, et al., *J. Antimicrob. Chemother.* 40:605–607, 1997) reported all 19 unspecieted clostridial isolates they studied to be susceptible to ≤ 2 ug/ml.

The data presented herein shows that there is marked variation in susceptibility patterns of different anaerobic genera and species to trovafloxacin and gemifloxacin and that important clinical anaerobic isolates should have individual strain susceptibilities determined. It is difficult to predict susceptibility based on a grouping of several species in a less commonly encountered or identified genus, and this problem has been solved in the methods of the invention.

Gemifloxacin exhibited good activity against Gram-positive anaerobes, especially the four Peptostreptococcus species tested, as well as the Porphyromonas species tested.

As provided herein, activities of gemifloxacin and comparator antimicrobial agents were determined by an agar dilution method against 419 clinical strains of less commonly identified, though medically important, species of anaerobes. Gemifloxacin was generally more active than trovafloxacin against Gram-positive strains by one to two dilutions. Peptostreptococci [*P. asaccharolyticus, P. magnus, P. micros,* and *P. prevotii*] and Porphyromonas spp. [*P. asaccharolytica, P. canoris, P. gingivalis, P. macaccae*] were all susceptible to ≤ 0.25 ug/ml of gemifloxacin. *Actinomyces israelii, Actinomyces odontolyticus, Clostridium innocuum, Clostridium clostridioforme,* Anaerobiospirillum spp.,*Bacteroides tectum, B. ureolyticus, B. gracilis* [now *Campylobacter gracilis*], *Prevotella intermedia, Prevotelia heparinolytica, Prevotella orisbuccae* group had MIC$_{90}$s of ≤ 2 μg/ml. *Fusobacterium naviforme* and *F. necrophorum* were also susceptible to ≤ 2 μg/ml, while *F. varium* strains exhibited a bimodal pattern; the other Fusobacterium species, such as *F. ulcerans, F. russii,* as well as Veillonella spp., *Prevotella melaninogenica* group, *P. bivia, Clostridium difficile,* and *Bilophila wadsworthia* were relatively resistant to gemifloxacin [MIC$_{90}$s ≥ 4 μg/ml].(See Table 1).

TABLE 1

In vitro activity [ug/ml] gemifloxacin, trovafloxacin, and other oral antimicrobial agents against unusual anaerobic pathogens.

| Minimal Inhibitory Concentration Organism & Agent (no. isolates)$^A$ | Range | 50% | 90% |
| --- | --- | --- | --- |
| *Actinomyces odontolyticus* [10] | | | |
| Gemifloxacin | 1–2 | 2 | 2 |
| Trovafloxacin | 2–4 | 4 | 4 |
| Penicillin G | 0.125–0.25 | 0.125 | .0125 |
| Amoxicillin clavulanate | 0.06–0.125 | 0.125 | 0.25 |
| Clindamycin | ≤0.015–0.5 | 0.125 | 0.25 |
| Erythromycin | ≤0.015–0.03 | ≤0.015 | 0.03 |
| Azithromycin | ≤0.015–0.06 | 0.03 | 0.06 |
| Clarithromycin | ≤0.015 | ≤0.015 | ≤0.015 |
| Metronidazole | 4–>32 | 16 | 32 |
| *Actinomyces israelii* [6] | | | |
| Gemifloxacin | 0.5–2 | 1 | |
| Trovafloxacin | 0.5–2 | 1 | |
| Penicillin G | ≤0.015–0.25 | 0.03 | |
| Amoxicillin clavulanate | 0.03–1 | 0.03 | |
| Clindamycin | 0.06–0.25 | 0.06 | |
| Erythromycin | 0.03 | 0.03 | |

TABLE 1-continued

In vitro activity [ug/ml] gemifloxacin, trovafloxacin, and other oral antimicrobial agents against unusual anaerobic pathogens.

| Minimal Inhibitory Concentration Organism & Agent (no. isolates)[A] | Range | 50% | 90% |
|---|---|---|---|
| Azithromycin | 0.06 | 0.06 | |
| Clarithromycin | ⇔0.015 | ⇔0.015 | |
| Metronidazole | 1–32 | 4 | |
| *Anaerobiospirillum thomasii* [13] | | | |
| Gemifloxacin | 0.06–0.25 | 0.125 | 0.125 |
| Trovafloxacin | 0.06–0.5 | 0.125 | 0.25 |
| Penicillin G | 0.06–0.125 | 0.06 | 0.125 |
| Amoxicillin clavulanate | 0.125–0.25 | 0.125 | 0.25 |
| Clindamycin | 8–>32 | 32 | >32 |
| Erythromycin | 1–16 | 4 | 8 |
| Azithromycin | 0.125–2 | 0.5 | 1 |
| Clarithromycin | 2–32 | 4 | 16 |
| Metronidazole | 1–4 | 2 | 4 |
| *Anaerobiospirillum succiniciproducens* [33] | | | |
| Gemifloxacin | 0.5–2 | 1 | |
| Trovafloxacin | 0.5–2 | 1 | |
| Penicillin G | 0.5–1 | 0.5 | |
| Amoxicillin clavulanate | 0.25–0.5 | 0.25 | |
| Clindamycin | 32 | 32 | |
| Erythromycin | 8–16 | 16 | |
| Azithromycin | 0.5–1 | 0.5 | |
| Clarithromycin | 8–32 | 32 | |
| Metronidazole | 4–8 | 8 | |
| *Bacteroides gracilis* [11] | | | |
| Gemifloxacin | ⇔0.015–1 | ⇔0.015 | 1 |
| Trovofloxacin | ⇔0.015–2 | 0.03 | 0.5 |
| Penicillin G | ⇔0.015–4 | 0.125 | 4 |
| Amoxicillin clavulanate | 0⇔.015–2 | 0.5 | 2 |
| Clindamycin | 0.03–8 | 0.25 | 2 |
| Erythromycin | 0.125–2 | 1 | 2 |
| Azithromycin | 0.06–0.5 | 0.125 | 0.5 |
| Clarithromycin | 0.25–2 | 1 | 1 |
| Metronidazole | 0.06 > 32 | 0.5 | >32 |
| *Bacteroides tectum* [22] | | | |
| Gemifloxacin | 0.06–8 | 0.125 | 0.25 |
| Trovafloxacin | 0.03–0.125 | 0.06 | 0.125 |
| Penicillin G | ⇔0.015–32 | 0.03 | 16 |
| Amoxicillin clavulanate | 0.03–0.5 | 0.06 | 0.5 |
| Clindamycin | ⇔0.015–0.12 | ⇔0.015 | ⇔0.015 |
| Erythromycin | 0.25–1 | 0.5 | 0.5 |
| Azithromycin | 0.5–2 | 1 | 2 |
| Clarithromycin | 0.125 | 0.125 | 0.125 |
| Metronidazole | 0.125–2 | 0.5 | 0.5 |
| *Bacteroides ureolyticus* [17] | | | |
| Gemifloxacin | ⇔0.015–2 | ⇔0.015 | 2 |
| Trovafloxacin | ⇔0.015–4 | 0.06 | 4 |
| Penicillin G | ⇔0.015–1 | ⇔0.015 | 0.25 |
| Amoxicillin clavulanate | ⇔0.015–1 | ⇔0.015 | 0.125 |
| Clindamycin | 0.03–0.5 | 0.06 | 0.25 |
| Erythromycin | 0.125–2 | .025 | 2 |
| Azithromycin | 0.06–0.25 | 0.06 | 0.25 |
| Clarithromycin | 0.125–4 | 0.5 | 2 |
| Metronidazole | 0.06–2 | 0.25 | 1 |
| *Bilophila wadsworthia* [16] | | | |
| Gemifloxacin | 0.125–>8 | 0.25 | 4 |
| Trovafloxacin | 0.125–>8 | 0.5 | >8 |
| Penicillin G | 2–16 | 4 | 8 |
| Amoxicillin clavulanate | 1–4 | 2 | 4 |
| Clindamycin | 0.25–2 | 0.5 | 2 |
| Erythromycin | 4–32 | 16 | 32 |
| Azithromycin | 1–16 | 4 | 16 |
| Clarithromycin | 4–32 | 16 | 32 |
| Metronidazole | 0.125 | 0.125 | 0.125 |
| *Clostridium clostridioforme* [11] | | | |
| Gemifloxacin | 0.5–> 8 | 0.5 | 1 |
| Trovafloxacin | 1–8 | 4 | 4 |
| Penicillin G | 0.5–> 32 | 1 | 16 |
| Amoxicillin clavulanate | 0.5–8 | 0.5 | 1 |
| Clindamycin | ⇔0.015–2 | 0.06 | 2 |
| Erythromycin | 0.25–> 32 | 16 | >32 |
| Azithromycin | 0.125–> 32 | 16 | >32 |
| Clarithromycin | 0.125–> 32 | 4 | >32 |
| Metronidazole | 0.03–1 | 0.125 | 0.5 |
| *Clostridium difficile* [14] | | | |
| Gemifloxacin | 1–> 8 | 2 | >8 |
| Trovafloxacin | 0.5–> 8 | 1 | >8 |
| Penicillin G | 1–4 | 2 | 4 |
| Amoxicillin clavulanate | 0.5–1 | 1 | 1 |
| Clindamycin | 0.25–> 32 | 0.5 | >32 |
| Erythromycin | 0.25 > 32 | 0.5 | >32 |
| Azithromycin | 1–> 32 | 2 | >32 |
| Clarithromycin | 0.125–> 32 | 0.5 | >32 |
| Metronidazole | 0.25–1 | 0.5 | 0.5 |
| *Clostridium inocuum* [11] | | | |
| Gemifloxacin | 0.125–> 8 | 0.25 | 2 |
| Trovafloxacin | 0.25–> 8 | 0.5 | 8 |
| Penicillin G | 0.25–> 3 | 0.5 | 0.5 |
| Amoxicillin clavulanate | 0.5–2 | 0.5 | 0.5 |
| Clindamycin | 0.25–> 32 | 0.5 | >32 |
| Erythromyccin | 0.5–> 32 | >32 | >32 |
| Azithromycin | 0.125–> 32 | >32 | >32 |
| Clarithromycin | 0.25–> 32 | >32 | >32 |
| Metronidazole | 0.5–2 | 0.5 | 1 |
| *Clostridium ramosum* [10] | | | |
| Gemifloxacin | 0.125–2 | 0.25 | 1 |
| Trovafloxcin | 0.25–8 | 0.5 | 2 |
| Penicillin G | 0.06–1 | 0.06 | 1 |
| Amoxicillin clavulanate | 0.06–0.25 | 0.06 | 0.25 |
| Clindamycin | 0.25–4 | 2 | 2 |
| Erythromycin | 0.5–> 32 | 1 | >32 |
| Azithromycin | 0.125–> 32 | 0.25 | >32 |
| Clarithromycin | 0.25–> 32 | 0.5 | >32 |
| Metronidazole | 1 | 1 | 1 |
| *Fusobacterium* spp group 1 [19][B] | | | |
| Gemifloxacin | 0.06–8 | 0.25 | 8 |
| Trovafloxacin | 0.25–4 | 0.5 | 4 |
| Penicillin G | ⇔0.015–16 | ⇔0.015 | 2 |
| Amoxicillin clavulanate | ⇔0.015–0.25 | 0.06 | 0.125 |
| Clindamycin | ⇔0.015–2 | 0.06 | 0.125 |
| Erythromycin | 1–> 32 | 8 | 32 |
| Azithromycin | 0.06–32 | 1 | 8 |
| Clarithromycin | ⇔0.015–32 | 8 | 32 |
| Metronidazole | 0.125–0.5 | 0.25 | 4 |
| *Fusobacterium* spp. group 2 [12][C] | | | |
| Gemifloxacin | 0.125–> 8 | 4 | 4 |
| Trovafloxacin | 1–> 8 | 4 | 4 |
| Penicillin G | ⇔0.015–>32 | 0.25 | 0.5 |
| Amoxicillin clavulanate | 0.125–> 4 | 1 | 2 |
| Clindamycin | 0.06–8 | 1 | 8 |
| Erythromycin | 8–> 32 | >32 | >32 |
| Azithromycin | 1–> 32 | 16 | 32 |
| Clarithromycin | 4–> 32 | >32 | >32 |
| Metronidazole | 0.125–1 | 0.5 | 1 |
| *Fusobacterium russii* | | | |
| Gemifloxacin | 0.5–> 8 | >8 | >8 |
| Trovafloxacin | 0.5–4 | 4 | 4 |

TABLE 1-continued

In vitro activity [ug/ml] gemifloxacin, trovafloxacin, and other oral antimicrobial agents against unusual anaerobic pathogens.

| Minimal Inhibitory Concentration Organism & Agent (no. isolates)[A] | Range | 50% | 90% |
|---|---|---|---|
| Penicillin G | ⇔0.015–0.06 | 0.03 | 0.06 |
| Amoxicillin clavulanate | ⇔0.015–0.25 | 0.06 | 0.125 |
| Clindamycin | ⇔0.015–0.125 | 0.03 | 0.06 |
| Erythromycin | 1–>32 | 4 | >32 |
| Azithromycin | 0.03–32 | 0.25 | 32 |
| Clarithromycin | 2–>32 | 4 | >32 |
| Metronidazole | ⇔0.015–0.25 | 0.125 | 0.25 |
| *Fusobacterium varium* [17] | | | |
| Gemifloxacin | 0.25–>8 | >8 | >8 |
| Trovafloxacin | 0.5–>8 | 4 | >8 |
| Penicillin G | 0.03–>32 | 0.5 | 8 |
| Amoxicillin clavulanate | 0.125–4 | 2 | 4 |
| Clindamycin | 0.06–16 | 4 | 16 |
| Erythromycin | 32–>32 | >32 | >32 |
| Azithromycin | 2–>32 | 32 | >32 |
| Clarithromycin | 32–>32 | >32 | >32 |
| Metronidazole | 0.125–4 | 1 | 2 |
| *Peptostreptococcus asaccharolyticus* [11] | | | |
| Gemifloxacin | 0.125–0.25 | 0.25 | 0.25 |
| Trovafloxacin | 0.5–2 | 1 | 1 |
| Penicillin G | ⇔0.015–1 | 0.03 | 0.25 |
| Amoxicillin clavulanate | 0.03–1 | 0.03 | 0.125 |
| Clindamycin | ⇔0.015–>32 | 0.06 | >32 |
| Erythromycin | 1–>32 | 4 | >32 |
| Azithromycin | 0.5–>32 | 4 | >32 |
| Clarithromycin | 0.5–>32 | 2 | >32 |
| Metronidazole | 0.125–2 | 0.5 | 1 |
| *Peptostreptococcus magnus* [13] | | | |
| Gemifloxacin | 0.030.03 | 0.03 | 0.06 |
| Trovafloxacin | 0.06–0.25 | 0.125 | 0.25 |
| Penicillin G | ⇔0.015–1 | 0.03 | 0.25 |
| Amoxicillin clavulanate | 0.03–1 | 0.03 | 0.125 |
| Clindamycin | 0.06–2 | 0.5 | 2 |
| Erythromycin | 1–>32 | 4 | >32 |
| Azithromycin | 2–>32 | 4 | >32 |
| Clarithromycin | 0.5–>32 | 2 | >32 |
| Metronidazole | 0.25–2 | 0.5 | 0.5 |
| *Peptostreptoeoccus micros* [12] | | | |
| Gemifloxacin | 0.06–0.125 | 0.06 | 0.06 |
| Trovafloxacin | 0.03–0.125 | 0.06 | 0.06 |
| Penicillin G | ⇔0.015–0.03 | ⇔0.015 | 0.03 |
| Amoxicillin clavulanate | 0.03–0.125 | 0.03 | 0.125 |
| Erythromycin | 0.5–1 | 0.5 | 0.5 |
| Azithromycin | 0.5–1 | 0.5 | 1 |
| Clarithromycin | 0.6 | 0.5 | 0.5 |
| Clindamycin | 0.06–0.125 | 0.125 | 0.125 |
| Metronidazole | 0.03–0.25 | 0.25 | 0.25 |
| *Peptostreptococcus prevotii* [9] | | | |
| Gemifloxacin | 0.06–0.25 | 0.125 | — |
| Trovafloxacin | 0.25–1 | 0.25 | — |
| Penicillin G | 0.03–0.06 | 0.03 | — |
| Amoxicillin clavulanate | ⇔0.015–0.125 | 0.03 | — |
| Clindamycin | 0.030–32 | 1 | — |
| Erythromycin | 0.03–>32 | >32 | — |
| Azithromycin | 0.06–>32 | 32 | — |
| Clarithromycin | ⇔0.015–>32 | >32 | — |
| Metronidazole | 0.125–1 | 0.5 | — |
| *Porphyromonas asaccharolyticus* [11] | | | |
| Gemifloxacin | 0.06–0.125 | 0.06 | 0.125 |
| Trovafloxacin | 0.03–0.25 | 0.25 | 0.25 |
| Penicillin G | ⇔0.015 | ⇔0.015 | ⇔0.015 |
| Amoxicillin clavulanate | ⇔0.015–0.03 | ⇔0.015 | 0.03 |
| Clindamycin | ⇔0.015–>32 | ⇔0.015 | >32 |
| Erythromycin | 0.03–32 | 0.03 | 32 |
| Azithromycin | 0.125–>32 | 0.25 | >32 |
| Clarithromycin | ⇔0.015–>32 | 0.06 | >32 |
| Metronidazole | ⇔0.015 | ⇔0.015 | ⇔0.015 |
| *Porphyromonas canoris* [10] | | | |
| Gemifloxacin | 0.06–0.25 | 0.25 | 0.25 |
| Trovafloxacin | 0.06–0.5 | 0.25 | 0.5 |
| Penicillin G | ⇔0.015–0.03 | ⇔0.015 | ⇔0.015 |
| Amoxicillin clavulanate | ⇔0.015–0.03 | ⇔0.015 | 0.03 |
| Clindamycin | ⇔0.015 | ⇔0.015 | ⇔0.015 |
| Erythromycin | 0.03–0.25 | 0.06 | 0.125 |
| Azithromycin | 0.125–0.5 | 0.25 | 0.25 |
| Clarithromycin | 0.06–0.125 | 0.06 | 0.125 |
| Metronidazole | ⇔0.015–0.5 | 0.25 | 0.25 |
| *Porphyromonas gingivalis* [13] | | | |
| Gemifloxacin | ⇔0.015–0.125 | 0.06 | 0.125 |
| Trovafloxacin | 0.03–0.06 | 0.06 | 0.06 |
| Penicillin G | ⇔0.015–0.06 | ⇔0.015 | 0.03 |
| Amoxicillin clavulanate | ⇔0.015–0.06 | ⇔0.015 | 0.06 |
| Clindamycin | ⇔0.015 | ⇔0.015 | ⇔0.015 |
| Erythromycin | 0.06–0.5 | 0.125 | 0.5 |
| Azithromycin | 0.125–1 | 0.25 | 0.5 |
| Clarithromycin | 0.06–0.125 | 0.06 | 0.125 |
| Metronidazole | ⇔0.015–0.03 | ⇔0.015 | 0.03 |
| *Porphyrotnonas macaccae* [13] | | | |
| Gemifloxacin | 0.03–0.125 | 0.06 | 0.125 |
| Trovafloxacin | 0.03–0.125 | 0.06 | 0.125 |
| Penicillin G | ⇔0.015–1 | 0.5 | 0.5 |
| Amoxicillin clavulanate | ⇔0.015–0.06 | ⇔0.015 | ⇔0.015 |
| Clindamycin | ⇔0.015–0.03 | ⇔0.015 | ⇔0.015 |
| Erythromycin | 0.06–0.25 | 0.125 | 0.25 |
| Azithromycin | 0.125–1 | 0.5 | 0.5 |
| Clarithromycin | 0.06–0.125 | 0.125 | 0.125 |
| Metronidazole | ⇔0.015–0.125 | 0.06 | 0.125 |
| *Porphymmonas* spp. [11][D] | | | |
| Gemifloxacin | 0.06–0.125 | 0.06 | 0.125 |
| Trovafloxacin | 0.06–1 | 0.25 | 1 |
| Penicillin G | ⇔0.015–4 | ⇔0.015 | ⇔0.015 |
| Amoxicillin clavulanate | ⇔0.015–0.06 | ⇔0.015 | ⇔0.015 |
| Clindamycin | ⇔0.015 | ⇔0.015 | ⇔0.015 |
| Erythromycin | ⇔0.015–0.5 | 0.06 | 0.06 |
| Azithromycin | 0.125–1 | 0.25 | 0.5 |
| Clarithromycin | 0.06–0.125 | 0.06 | 0.125 |
| Metronidazole | ⇔0.015–0.25 | 0.03 | 0.125 |
| *Prevotella bivia* [21] | | | |
| Gemifloxacin | 4–>8 | 8 | 8 |
| Trovafloxacin | 1–4 | 2 | 2 |
| Penicillin G | 0.25–32 | 16 | 32 |
| Amoxicillin clavulanate | 0.06–4 | 0.5 | 4 |
| Clindamycin | ⇔0.015–>32 | ⇔0.015 | 0.03 |
| Erythromycin | 0.06–>32 | 1 | 2 |
| Azithromycin | 0.25–>32 | 0.5 | 1 |
| Clarithromycin | 0.06–>32 | 0.125 | 0.25 |
| Metronidazole | 0.5–4 | 2 | 4 |

TABLE 1-continued

In vitro activity [ug/ml] gemifloxacin, trovafloxacin, and other oral antimicrobial agents against unusual anaerobic pathogens.

| Minimal Inhibitory Concentration Organism & Agent (no. isolates)[A] | Range | 50% | 90% |
|---|---|---|---|
| *Prevotella buccae-oris* group [22][E] | | | |
| Gemifloxacin | 0.5–8 | 2 | 2 |
| Trovafloxacin | 0.25–4 | 1 | 2 |
| Penicillin G | 0.06–>32 | 8 | >32 |
| Amoxicillin clavulanate | 0.125–2 | 0.25 | 1 |
| Erythromycin | 0.5–8 | 1 | 2 |
| Azithromycin | 0.125–4 | 0.5 | 1 |
| Clarithromycin | 0.06–1 | 0.125 | 0.25 |
| Clindamycin | ⇔0.015–0.12 | ⇔0.015 | 0.03 |
| Metronidazole | 0.5–4 | 1 | 2 |
| *Prevotella heparinolytica* [16] | | | |
| Gemifloxacin | 0.25–0.5 | 0.5 | 0.5 |
| Trovafloxacin | 0.125–0.25 | 0.125 | 0.25 |
| Penicillin G | 0.06–0.25 | 0.06 | 0.125 |
| Amoxicillin clavulanate | 0.06–0.25 | 0.125 | 0.25 |
| Clindamycin | ⇔0.015 | ⇔0.015 | ⇔0.015 |
| Erythromycin | 0.25–0.5 | 0.25 | 0.25 |
| Azithromycin | 0.5–1 | 0.5 | 1 |
| Clarithromycin | 0.06–0.125 | 0.125 | 0.125 |
| Metronidazole | 0.06–1 | 0.5 | 1 |
| *Prevotella intermedia* [11] | | | |
| Gemifloxacin | 0.06–1 | 0.25 | 0.5 |
| Trovafloxacin | 0.06–1 | 0.5 | 1 |
| Penicillin G | ⇔0.015–16 | 0.03 | 4 |
| Amoxicillin clavulanate | 0.03–0.5 | 0.03 | 0.125 |
| Clindamycin | ⇔0.015–0.03 | ⇔0.015 | ⇔0.015 |
| Erythromycin | 0.03–0.5 | 0.06 | 0.25 |
| Azithromycin | 0.03–1 | 0.125 | 0.5 |
| Clarithromycin | ⇔0.015–0.12 | ⇔0.015 | 0.125 |
| Metronidazole | 0.03–1 | 0.5 | 1 |
| *Prevotella melaninogenica* [12] | | | |
| Gemifloxacin | 0.125–>8 | 1 | 8 |
| Trovafloxacin | 0.06–8 | 1 | 4 |
| Penicillin G | ⇔0.015–2 | 0.25 | 2 |
| Amoxicillin clavulanate | 0.03–16 | 2 | 4 |
| Clindamycin | ⇔0.015–32 | ⇔0.015 | 0.5 |
| Erythromycin | 0.06–32 | 1 | 8 |
| Azithromycin | 0.125–>32 | 0.25 | 32 |
| Clarithromycin | 0.06–4 | 0.125 | 1 |
| Metronidazole | 0.125–4 | 0.5 | 1 |
| *Prevotella denticola/loeschii* group [6] | | | |
| Gemifloxacin | 0.25–8 | 0.5 | |
| Trovofloxacin | 0.06–4 | 1 | |
| Penicillin G | ⇔0.015–32 | 4 | |
| Amoxicillin clavulanate | 0.03–0.5 | 0.06 | |
| Clindamycin | ⇔0.015–0.25 | ⇔0.015 | |
| Erythromycin | 0.125–16 | 0.25 | |
| Azithromycin | 0.06–16 | 0.5 | |
| Clarithromycin | 0.03–2 | 0.06 | |
| Metronidazole | 0.5–1 | 1 | |
| *Veillonella* spp. [24] | | | |
| Gemifloxacin | 0.03–>8 | 1 | 8 |
| Trovafloxacin | 0.125–>8 | 0.25 | >8 |
| Penicillin G | ⇔0.015–8 | 1 | 4 |
| Amoxicillin clavulanate | ⇔0.015–>4 | 0.5 | 2 |
| Clindamycin | 0.03–>32 | 0.06 | 2 |
| Erythromycin | 1–>32 | 16 | >32 |
| Azithromycin | 0.125–>32 | 4 | >32 |
| Clarithromycin | 1–>32 | 16 | >32 |
| Metronidazole | 0.25–2 | 1 | 2 |

[A]MIC$_{50}$, MIC$_{90}$-Minimal inhibitory concentration for 50% and 90% of isolates tested, respectively
[B]-*Fusobacterium gonidiaformans*, 1; *Fusobacterium naviforme*, 8; *Fusobacterium necrophorum*, 8; *Fusobacterium nucleatum*, 1; *Fusobacterium nucleatum ss animalis*, 1.
[C]-*Fusobacterium mortiferum*, 2; *Fusobactenum necrogenes*, 3; *Fusobacterium ulcerans*, 7.
[D]-*Porphyromonas cangingivalis*, 4; *Porphyromonas cansulci*, 2; *Porphyromonas circumdentaria*, 2; *Porphyromonas levii*, 3.
[E]-*Prevotella buccae*, 20; *Prevotella oris*, 2.

The invention provides a method for modulating metabolism of anaerobic pathogenic bacteria. Skilled artisans can readily choose anaerobic pathogenic bacteria or patients infected with or suspected to be infected with these organisms to practice the methods of the invention. Alternatively, the bacteria useful in the methods of the invention may be those described herein.

The contacting step in any of the methods of the invention may be performed in many ways that will be readily apparent to the skilled artisan. However, it is preferred that the contacting step is a provision of a composition comprising a gemifloxacin compound to a human patient in need of such composition or directly to bacteria in culture medium or buffer.

For example, when contacting a human patient or contacting said bacteria in a human patient or in vitro, the compositions comprising a quinolone, particularly a gemifloxacin compound, preferably pharmaceutical compositions may be administered in any effective, convenient manner including, for instance, administration by topical, oral, anal, vaginal, intravenous, intraperitoneal, intramuscular, subcutaneous, intranasal or intradermal routes among others.

It is also preferred that these compositions be employed in combination with a non-sterile or sterile carrier or carriers for use with cells, tissues or organisms, such as a pharmaceutical carrier suitable for administration to a subject. Such compositions comprise, for instance, a media additive or a therapeutically effective amount of a compound of the invention, a quinolone, preferably a gemifloxacin compound, and a pharmaceutically acceptable carrier or excipient. Such carriers may include, but are not limited to, saline, buffered saline, dextrose, water, glycerol, ethanol and combinations thereof. The formulation should suit the mode of administration.

Quinolone compounds, particularly gemifloxacin compounds and compostions of the methods of the invention may be employed alone or in conjunction with other compounds, such as bacterial efflux pump inhibtor compounds or antibiotic compounds, particularly non-quinolone compounds, e.g., beta-lactam antibiotic compounds.

In therapy or as a prophylactic, the active agent of a method of the invention is preferably administered to an individual as an injectable composition, for example as a sterile aqueous dispersion, preferably an isotonic one.

Alternatively, the gemifloxacin compounds or compositions in the methods of the invention may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

For administration to mammals, and particularly humans, it is expected that the antibacterially effective amount is a daily dosage level of the active agent from 0.001 mg/kg to 10 mg/kg, typically around 0.1 mg/kg to 1 mg/kg, preferably about 1 mg/kg. A physician, in any event, will determine an actual dosage that is most suitable for an individual and will vary with the age, weight and response of the particular individual. The above dosages are exemplary of the average case. There can, of course, be individual instances where higher or lower dosage ranges are merited, and such are within the scope of this invention. It is preferred that the dosage is selected to modulate metabolism of the bacteria in such a way as to inhibit or stop growth of said bacteria or by killing said bacteria. The skilled artisan may identify this amount as provided herein as well as using other methods known in the art, e.g. by the application MIC tests.

A further embodiment of the invention provides for the contacting step of the methods to further comprise contacting an in-dwelling device in a patient. In-dwelling devices include, but are not limited to, surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, and continuous ambulatory peritoneal dialysis (CAPD) catheters.

A quinolone, particularly a gemifloxacin compound or composition of the invention may be administered by injection to achieve a systemic effect against relevant bacteria, preferably a anaerobic pathogenic bacteria, shortly before insertion of an in-dwelling device. Treatment may be continued after surgery during the in-body time of the device. In addition, the composition could also be used to broaden perioperative cover for any surgical technique to prevent bacterial wound infections caused by or related to anaerobic pathogenic bacteria.

In addition to the therapy described above, a gemifloxacin compound or composition used in the methods of this invention may be used generally as a wound treatment agent to prevent adhesion of bacteria to matrix proteins, particularly anaerobic pathogenic bacteria, exposed in wound tissue and for prophylactic use in dental treatment as an alternative to, or in conjunction with, antibiotic prophylaxis.

Alternatively, a quinolone, particularly a gemifloxacin compound or composition of the invention may be used to bathe an indwelling device immediately before insertion. The active agent will preferably be present at a concentration of 1 µg/ml to 10 mg/ml for bathing of wounds or indwelling devices.

Also provided by the invention is a method of treating or preventing a bacterial infection by anaerobic pathogenic bacteria comprising the step of administering an antibacterially effective amount of a composition comprising a quinolone, particularly a gemifloxacin compound to a mammal, preferably a human, suspected of having or being at risk of having an infection with anaerobic pathogenic bacteria.

While a preferred object of the invention provides a method wherein said anaerobic pathogenic bacteria is selected from the group consisting of: selected from the group consisting of: a member of the genus Peptostreptococci, a Peptostreptococci asaccharolyticus, a Peptostreptococci magnus, a Peptostreptococci micros, a Peptostreptococci prevotii, a member of the genus Porphyromonas, a Porphyromonas asaccharolytica, a Porphyromonas canoris, a Porphyromonas gingivalis, a Porphyromonas macaccae, a member of the genus Actinomyces, an Actinomyces israelii, an Actinomyces odontolyticus, a member of the genus Clostridium, a Clostridium innocuum, a Clostridium clostridioforme, a Clostridium difficile, a member of the genus Anaerobiospirillum, a member of the genus Bacteroides, a Bacteroides tectum, a Bacteroides ureolyticus, a Bacteroides gracilis (Campylobacter gracilis), a member of the genus Prevotella, a Prevotella intermedia, a Prevotella heparinolytica, a Prevotelia oris-buccae, a Prevotella bivia, a Prevotella melaninogenica, a member of the genus Fusobacterium, a Fusobacterium naviforme, a Fusobacterium necrophorum, a Fusobacterium varium, a Fusobacterium ulcerans, a Fusobacterium russii, a member of the genus Bilophila, a Bilophila wadsworthia.

Other anaerobic pathogenic bacteria may also be included in the methods. The skilled artisan may identify these organisms as provided herein as well as using other methods known in the art, e.g. MIC tests.

Preferred embodiments of the invention include, among other things, methods wherein said composition comprises gemifloxacin, or a pharmaceutically acceptable derivative thereof.

EXAMPLES

The present invention is further described by the following examples. The examples are provided solely to illustrate the invention by reference to specific embodiments. This exemplification's, while illustrating certain specific aspects of the invention, do not portray the limitations or circumscribe the scope of the disclosed invention.

All examples were carried out using standard techniques, which are well known and routine to those of skill in the art, except where otherwise described in detail.

All parts or amounts set out in the following examples are by weight, unless otherwise specified.

Example 1 Bacterial Strains

The strains were previously isolated from human clinical specimens from a variety of sources, and were identified by standard criteria (Alexander, et al., J. Clin. Microbiol., 35:406–411, 1997; Citron, et al., Clin. Infect. Dis., 23 (Suppl. 1): 78–82, 1996; Holdeman, et al., Anaerobic Laboratory Manual, 4th Edition, 1977; Summanen, et al., Wadsworth Anaerobic Bacteriology Manual, 5th Edition, 1993). Almost all these isolates were different from those strains used in our prior study (Goldstein, et al., Antimicrob. Agents Chemother., Submitted] when we used the same genus and species. Bacteroides fragilis ATCC 25285, and Bacteroides thetaiotaomicron ATCC 29741 were tested simultaneously as control strains. The numbers and species of isolates tested are given in Table 1.

Example 1 Compounds

Frozen cultures were transferred at least twice on Brucella agar supplemented with hemin, vitamin $K_1$, and 5% sheep blood to ensure purity and good growth. Susceptibility testing was performed according to National Committee for Clinical Laboratory Standards (NCCLS) standards (*National Committee for Clinical Laboratory Standards,* 4th Edition, 1997). Brucella agar supplemented with hemin, vitamin $K_1$ and 5% laked sheep blood was the basal medium used. For *Bilophila wadsworthia,* the agar was also supplemented with pyruvate. Antimicrobial agents were reconstituted according to the manufacturers' instructions. Serial twofold dilutions of antimicrobial agents were prepared on the day of the test and added to the media in varying concentrations (μg/ml). The agar plates were inoculated with a Steers replicator (Craft Machine Inc., Chester, Pa.). The inoculum used was $10^5$ CFU per spot. Control plates without antimicrobial agents were inoculated before and after each set of drug-containing plates. The MIC was defined as the lowest concentration of an agent that yielded no growth, or a marked change in the appearance of growth as compared to the growth control plate.

Each reference cited herein is hereby incorporated by reference in its entirety. Moreover, each patent application to which this application claims priority is hereby incorporated by reference in its entirety.

What is claimed is:

1. A method for modulating metabolism of anaerobic pathogenic bacteria comprising the step of contacting anaerobic pathogenic bacteria with an antibacterially effective amount of a composition comprising a gemifloxacin compound, or antibacterially effective derivatives thereof.

2. The method of claim 1 wherein said bacteria is selected from the group consisting of:

a member of the genus Peptostreptococci, a member of the genus Actinomyces, a member of the genus *Clostridium*, a member of the genus *Anaerobiospirillum*, a member of the genus Fusobacterium, and a member of the genus *Bilophila*.

3. The method of claim 1 wherein said modulating metabolism is inhibiting growth of said bacteria.

4. The method of claim 1 wherein said modulating metabolism is killing said bacteria.

5. The method of claim 1 wherein said contacting said bacteria comprises the further step of introducing said composition into a mammal.

6. The method of claim 5 wherein said mammal is a human.

7. The method of claim 1 wherein said bacteria is selected from the group consisting of:

*Peptostreptococci asaccharolyticus, Peptostreptococci magnus, Peptostreptococci micros, Peptostreptococci prevotii, Porphyromonas asaccharolytica,* a *Porphyromonas canoris, Porphyromonas gingivalis, Porphyromonas macaccae, Actinomyces israelii, Actinomyces odontolyticus, Clostridium innocuum, Clostridium clostridioforme, Clostridium difficile, Bacteroides tectum, Bacteroides ureolyticus, Bacteroides gracilis* (*Campylobacter gracilis*), *Prevotella intermedia, Prevotella heparinolytica, Prevotella oris-buccae, Prevotella bivia, Prevotella melaninogenica, Fusobacterium naviforme, Fusobacterium necrophorum, Fusobacterium varium, Fusobacterium ulcerans, Fusobacterium russii,* and *Bilophila wadsworthia.*

8. The method according to claim 1 wherein the gemifloxacin compound is gemifloxacin or a pharmaceutically acceptable salt thereof.

9. The method according to claim 8 wherein the gemifloxacin compound is gemifloxacin mesylate or a hydrate thereof.

10. The method according to claim 9 wherein the gemifloxacin compound is gemifloxacin mesylate sesquihydrate.

11. The method according to claim 2 wherein the gemifloxacin compound is gemifloxacin or a pharmaceutically acceptable salt thereof.

12. The method according to claim 7 wherein the gemifloxacin compound is gemifloxacin mesylate or a hydrate thereof.

13. The method according to claim 11 wherein the gemifloxacin compound is gemifloxacin mesylate or a hydrate thereof.

14. The method according to claim 12 wherein the gemifloxacin compound is gemifloxacin mesylate or hydrate thereof.

15. The method according to claim 13 wherein the gemifloxacin compound is gemifloxacin mesylate sesquihydrate.

16. The method according to claim 14 wherein the gemifloxacin compound is gemifloxacin mesylate sesquihydrate.

* * * * *